(12) United States Patent
Yokoi et al.

(10) Patent No.: US 7,078,204 B2
(45) Date of Patent: Jul. 18, 2006

(54) GLUCOSE-6-PHOSPHATE DEHYDROGENASE

(75) Inventors: Haruhiko Yokoi, Machida (JP); Seiko Ando, Machida (JP); Keiko Ochiai, Machida (JP); Yoshiyuki Yonetani, Machida (JP); Shin-ichi Hashimoto, Hofu (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 307 days.

(21) Appl. No.: 10/312,007

(22) PCT Filed: Jun. 15, 2001

(86) PCT No.: PCT/JP01/05113

§ 371 (c)(1),
(2), (4) Date: Dec. 23, 2002

(87) PCT Pub. No.: WO01/00844

PCT Pub. Date: Jan. 4, 2001

(65) Prior Publication Data

US 2004/0171130 A1 Sep. 2, 2004

(30) Foreign Application Priority Data

Jun. 21, 2000 (JP) .............................. 2000-185789

(51) Int. Cl.
C12N 9/04 (2006.01)
C12N 1/20 (2006.01)
C12P 21/04 (2006.01)
C12P 13/04 (2006.01)
C07H 21/04 (2006.01)

(52) U.S. Cl. ............... 435/190; 435/252.3; 435/320.1; 435/69.1; 435/71.1; 435/440; 435/106; 435/113; 435/115; 536/23.2; 536/23.7

(58) Field of Classification Search ............... 435/190, 435/252.3, 320.1, 252.33, 252.32, 71.1, 440, 435/6, 69.1, 106, 113, 115; 536/23.2, 23.1, 536/23.7; 530/350
See application file for complete search history.

(56) References Cited

U.S. PATENT DOCUMENTS

2003/0175911 A1* 9/2003 Hans et al. .................. 435/115

FOREIGN PATENT DOCUMENTS

| JP | 09-224661 | * | 9/1997 |
| JP | 9-224662 | | 9/1997 |
| WO | 01/04322 | | 1/2001 |

OTHER PUBLICATIONS

Sahm, et al., "Pathway Analysis and Metabolic Engineering in *Corynebacterium glutamicum*", Med. Fac. Landbouww., vol. 65, No. 3A (2000), pp. 221-229.
Sahm, et al., "Pathway Analysis and Metabolic Engineering in *Corynebacterium glutamicum*", Biol. Chem., vol. 381, No. 9/10 (2000), pp. 899-910.

* cited by examiner

Primary Examiner—Manjunath Rao
Assistant Examiner—Yong Pak
(74) Attorney, Agent, or Firm—Fitzpatrick, Cella, Harper & Scinto

(57) ABSTRACT

The present invention relates to a novel glucose-6-phosphate dehydrogenase (hereinafter referred to as "G6PD") derived from a bacterium belonging to the genus *Corynebacterium*, a DNA encoding the enzyme, a recombinant DNA comprising the DNA, a transformant comprising the recombinant DNA, a transformant comprising the DNA on its chromosome, and a process for producing L-amino acid or G6PD which comprises culturing the transformant.

According to the present invention, a modified G6PD and a DNA encoding the G6PD are obtained, and the productivity of L-amino acid by a microorganism can be improved by using the modified G6PD.

17 Claims, 2 Drawing Sheets

```
                       SEQUENCE LISTING

<160> NUMBER OF SEQ ID NOS: 12

<210> SEQ ID NO 1
<211> LENGTH: 1452
<212> TYPE: DNA
<213> ORGANISM: Corynebacterium glutamicum
<220> FEATURE:
<221> NAME/KEY: CDS
<222> LOCATION: (1)..(1452)

<400> SEQUENCE: 1 atg gtg atc ttc ggt gtc act ggc gac ttg gct cga aag aag ctg ctc    48
Met Val Ile Phe Gly Val Thr Gly Asp Leu Ala Arg Lys Lys Leu Leu
 1               5                  10                  15 ccc gcc att tat gat cta gca aac cgc gga ttg ctg ccc cca gga ttc    96
Pro Ala Ile Tyr Asp Leu Ala Asn Arg Gly Leu Leu Pro Pro Gly Phe
             20                  25                  30 tcg ttg gta ggt tac ggc cgc cgc gaa tgg tcc aaa gaa gac ttt gaa   144
Ser Leu Val Gly Tyr Gly Arg Arg Glu Trp Ser Lys Glu Asp Phe Glu
         35                  40                  45 aaa tac gta cgc gat gcc gca agt gct ggt gct cgt acg gaa ttc cgt   192
Lys Tyr Val Arg Asp Ala Ala Ser Ala Gly Ala Arg Thr Glu Phe Arg
     50                  55                  60 gaa aat gtt tgg gag cgc ctc gcc gag ggt atg gaa ttt gtt cgc ggc   240
Glu Asn Val Trp Glu Arg Leu Ala Glu Gly Met Glu Phe Val Arg Gly
 65                  70                  75                  80 aac ttt gat gat gat gca gct ttc gac aac ctc gct gca aca ctc aag   288
Asn Phe Asp Asp Asp Ala Ala Phe Asp Asn Leu Ala Ala Thr Leu Lys
                 85                  90                  95 cgc atc gac aaa acc cgc ggc acc gcc ggc aac tgg gct tac tac ctg   336
Arg Ile Asp Lys Thr Arg Gly Thr Ala Gly Asn Trp Ala Tyr Tyr Leu
            100                 105                 110 tcc att cca cca gat tcc ttc aca gcg gtc tgc cac cag ctg gag cgt   384
Ser Ile Pro Pro Asp Ser Phe Thr Ala Val Cys His Gln Leu Glu Arg
        115                 120                 125 tcc ggc atg gct gaa tcc acc gaa gaa gca tgg cgc cgc gtg atc atc   432
Ser Gly Met Ala Glu Ser Thr Glu Glu Ala Trp Arg Arg Val Ile Ile
    130                 135                 140 gag aag cct ttc ggc cac aac ctc gaa tcc gca cac gag ctc aac cag   480
Glu Lys Pro Phe Gly His Asn Leu Glu Ser Ala His Glu Leu Asn Gln
145                 150                 155                 160
```

-continued

| | |
|---|---|
| ctg gtc aac gca gtc ttc cca gaa tct tct gtg ttc cgc atc gac cac<br>Leu Val Asn Ala Val Phe Pro Glu Ser Ser Val Phe Arg Ile Asp His<br>                              165                        170                        175 | 528 |
| tat ttg ggc aag gaa aca gtt caa aac atc ctg gct ctg cgt ttt gct<br>Tyr Leu Gly Lys Glu Thr Val Gln Asn Ile Leu Ala Leu Arg Phe Ala<br>                180                        185                        190 | 576 |
| aac cag ctg ttt gag cca ctg tgg aac tcc aac tac gtt gac cac gtc<br>Asn Gln Leu Phe Glu Pro Leu Trp Asn Ser Asn Tyr Val Asp His Val<br>            195                        200                        205 | 624 |
| cag atc acc atg gct gaa gat att ggc ttg ggt gga cgt gct ggt tac<br>Gln Ile Thr Met Ala Glu Asp Ile Gly Leu Gly Gly Arg Ala Gly Tyr<br>210                        215                        220 | 672 |
| tac gac ggc atc ggc gca gcc cgc gac gtc atc cag aac cac ctg atc<br>Tyr Asp Gly Ile Gly Ala Ala Arg Asp Val Ile Gln Asn His Leu Ile<br>225                        230                        235                        240 | 720 |
| cag ctc ttg gct ctg gtt gcc atg gaa gaa cca att tct ttc gtg cca<br>Gln Leu Leu Ala Leu Val Ala Met Glu Glu Pro Ile Ser Phe Val Pro<br>                245                        250                        255 | 768 |
| gcg cag ctg cag gca gaa aag atc aag gtg ctc tct gcg aca aag ccg<br>Ala Gln Leu Gln Ala Glu Lys Ile Lys Val Leu Ser Ala Thr Lys Pro<br>            260                        265                        270 | 816 |
| tgc tac cca ttg gat aaa acc tcc gct cgt ggt cag tac gct gcc ggt<br>Cys Tyr Pro Leu Asp Lys Thr Ser Ala Arg Gly Gln Tyr Ala Ala Gly<br>        275                        280                        285 | 864 |
| tgg cag ggc tct gag tta gtc aag gga ctt cgc gaa gaa gat ggc ttc<br>Trp Gln Gly Ser Glu Leu Val Lys Gly Leu Arg Glu Glu Asp Gly Phe<br>    290                        295                        300 | 912 |
| aac cct gag tcc acc act gag act ttt gcg gct tgt acc tta gag atc<br>Asn Pro Glu Ser Thr Thr Glu Thr Phe Ala Ala Cys Thr Leu Glu Ile<br>305                        310                        315                        320 | 960 |
| acg tct cgt cgc tgg gct ggt gtg ccg ttc tac ctg cgc acc ggt aag<br>Thr Ser Arg Arg Trp Ala Gly Val Pro Phe Tyr Leu Arg Thr Gly Lys<br>                325                        330                        335 | 1008 |
| cgt ctt ggt cgc cgt gtt act gag att gcc gtg gtg ttt aaa gac gca<br>Arg Leu Gly Arg Arg Val Thr Glu Ile Ala Val Val Phe Lys Asp Ala<br>            340                        345                        350 | 1056 |
| cca cac cag cct ttc gac ggc gac atg act gta tcc ctt ggc caa aac<br>Pro His Gln Pro Phe Asp Gly Asp Met Thr Val Ser Leu Gly Gln Asn<br>        355                        360                        365 | 1104 |
| gcc atc gtg att cgc gtg cag cct gat gaa ggt gtg ctc atc cgc ttc<br>Ala Ile Val Ile Arg Val Gln Pro Asp Glu Gly Val Leu Ile Arg Phe<br>370                        375                        380 | 1152 |
| ggt tcc aag gtt cca ggt tct gcc atg gaa gtc cgt gac gtc aac atg<br>Gly Ser Lys Val Pro Gly Ser Ala Met Glu Val Arg Asp Val Asn Met<br>385                        390                        395                        400 | 1200 |
| gac ttc tcc tac tca gaa tcc ttc act gaa gaa tca cct gaa gca tac<br>Asp Phe Ser Tyr Ser Glu Ser Phe Thr Glu Glu Ser Pro Glu Ala Tyr<br>                405                        410                        415 | 1248 |
| gag cgc ctc att ttg gat gcg ctg tta gat gaa tcc agc ctc ttc cct<br>Glu Arg Leu Ile Leu Asp Ala Leu Leu Asp Glu Ser Ser Leu Phe Pro<br>            420                        425                        430 | 1296 |
| acc aac gag gaa gtg gaa ctg agc tgg aag att ctg gat cca att ctt<br>Thr Asn Glu Glu Val Glu Leu Ser Trp Lys Ile Leu Asp Pro Ile Leu<br>        435                        440                        445 | 1344 |
| gaa gca tgg gat gcc gat gga gaa cca gag gat tac cca gcg ggt acg<br>Glu Ala Trp Asp Ala Asp Gly Glu Pro Glu Asp Tyr Pro Ala Gly Thr<br>450                        455                        460 | 1392 |

```
tgg ggt cca aag agc gct gat gaa atg ctt tcc cgc aac ggt cac acc    1440
Trp Gly Pro Lys Ser Ala Asp Glu Met Leu Ser Arg Asn Gly His Thr
465                 470                 475                 480 tgg cgc agg cca                                                    1452
Trp Arg Arg Pro
```

<210> SEQ ID NO 2
<211> LENGTH: 484
<212> TYPE: PRT
<213> ORGANISM: Corynebacterium glutamicum

<400> SEQUENCE: 2

```
Met Val Ile Phe Gly Val Thr Gly Asp Leu Ala Arg Lys Lys Leu Leu
 1               5                  10                  15

Pro Ala Ile Tyr Asp Leu Ala Asn Arg Gly Leu Leu Pro Pro Gly Phe
            20                  25                  30

Ser Leu Val Gly Tyr Gly Arg Arg Glu Trp Ser Lys Glu Asp Phe Glu
        35                  40                  45

Lys Tyr Val Arg Asp Ala Ala Ser Ala Gly Ala Arg Thr Glu Phe Arg
    50                  55                  60

Glu Asn Val Trp Glu Arg Leu Ala Glu Gly Met Glu Phe Val Arg Gly
65                  70                  75                  80

Asn Phe Asp Asp Ala Ala Phe Asp Asn Leu Ala Ala Thr Leu Lys
                85                  90                  95

Arg Ile Asp Lys Thr Arg Gly Thr Ala Gly Asn Trp Ala Tyr Tyr Leu
            100                 105                 110

Ser Ile Pro Pro Asp Ser Phe Thr Ala Val Cys His Gln Leu Glu Arg
        115                 120                 125

Ser Gly Met Ala Glu Ser Thr Glu Glu Ala Trp Arg Arg Val Ile Ile
    130                 135                 140

Glu Lys Pro Phe Gly His Asn Leu Glu Ser Ala His Glu Leu Asn Gln
145                 150                 155                 160

Leu Val Asn Ala Val Phe Pro Glu Ser Ser Val Phe Arg Ile Asp His
                165                 170                 175

Tyr Leu Gly Lys Glu Thr Val Gln Asn Ile Leu Ala Leu Arg Phe Ala
            180                 185                 190

Asn Gln Leu Phe Glu Pro Leu Trp Asn Ser Asn Tyr Val Asp His Val
        195                 200                 205

Gln Ile Thr Met Ala Glu Asp Ile Gly Leu Gly Gly Arg Ala Gly Tyr
    210                 215                 220

Tyr Asp Gly Ile Gly Ala Ala Arg Asp Val Ile Gln Asn His Leu Ile
225                 230                 235                 240

Gln Leu Leu Ala Leu Val Ala Met Glu Glu Pro Ile Ser Phe Val Pro
                245                 250                 255

Ala Gln Leu Gln Ala Glu Lys Ile Lys Val Leu Ser Ala Thr Lys Pro
            260                 265                 270

Cys Tyr Pro Leu Asp Lys Thr Ser Ala Arg Gly Gln Tyr Ala Ala Gly
        275                 280                 285

Trp Gln Gly Ser Glu Leu Val Lys Gly Leu Arg Glu Glu Asp Gly Phe
    290                 295                 300

Asn Pro Glu Ser Thr Thr Glu Thr Phe Ala Ala Cys Thr Leu Glu Ile
305                 310                 315                 320

Thr Ser Arg Arg Trp Ala Gly Val Pro Phe Tyr Leu Arg Thr Gly Lys
                325                 330                 335
```

```
Arg Leu Gly Arg Arg Val Thr Glu Ile Ala Val Val Phe Lys Asp Ala
            340                 345                 350
Pro His Gln Pro Phe Asp Gly Asp Met Thr Val Ser Leu Gly Gln Asn
        355                 360                 365
Ala Ile Val Ile Arg Val Gln Pro Asp Glu Gly Val Leu Ile Arg Phe
    370                 375                 380
Gly Ser Lys Val Pro Gly Ser Ala Met Glu Val Arg Asp Val Asn Met
385                 390                 395                 400
Asp Phe Ser Tyr Ser Glu Ser Phe Thr Glu Glu Ser Pro Glu Ala Tyr
                405                 410                 415
Glu Arg Leu Ile Leu Asp Ala Leu Leu Asp Glu Ser Ser Leu Phe Pro
            420                 425                 430
Thr Asn Glu Glu Val Glu Leu Ser Trp Lys Ile Leu Asp Pro Ile Leu
        435                 440                 445
Glu Ala Trp Asp Ala Asp Gly Glu Pro Glu Asp Tyr Pro Ala Gly Thr
    450                 455                 460
Trp Gly Pro Lys Ser Ala Asp Glu Met Leu Ser Arg Asn Gly His Thr
465                 470                 475                 480
Trp Arg Arg Pro
```

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 3
gatccgatga ggctttggct ctgcgtggc                                      29

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 4
cttcattggt ggactcggta actgcagcg                                      29

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: synthetic
      oligomer

<400> SEQUENCE: 5
aattcgcggc cgctctagac tgcagcggcc gcgcatg                             37

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: synthetic
      oligomer -continued

```
<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 7
aaaaagatct cgacggatcg ttccactg                                        28

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 8
gtaaaacgac ggccatg                                                    17

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 9
cgagtcgact cgcgaagtag cacctgtcac ttttg                                35

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence : Synthetic
      DNA

<400> SEQUENCE: 10
tggggatccg caccaacaac tgcgatggtg gtc                                  33

<210> SEQ ID NO 11
<211> LENGTH: 1452
<212> TYPE: DNA
<213> ORGANISM: Corynebacterium glutamicum
<220> FEATURE:
<221> NAME/KEY: CDS
<222> LOCATION: (1)..(1452)

<400> SEQUENCE: 11 atg gtg atc ttc ggt gtc act ggc gac ttg gct cga aag aag ctg ctc      48
Met Val Ile Phe Gly Val Thr Gly Asp Leu Ala Arg Lys Lys Leu Leu
 1               5                  10                  15 ccc gcc att tat gat cta gca aac cgc gga ttg ctg ccc cca gga ttc      96
Pro Ala Ile Tyr Asp Leu Ala Asn Arg Gly Leu Leu Pro Pro Gly Phe
             20                  25                  30 tcg ttg gta ggt tac ggc cgc cgc gaa tgg tcc aaa gaa gac ttt gaa     144
Ser Leu Val Gly Tyr Gly Arg Arg Glu Trp Ser Lys Glu Asp Phe Glu
         35                  40                  45
```

-continued

| | | |
|---|---|---|
| aaa tac gta cgc gat gcc gca agt gct ggt gct cgt acg gaa ttc cgt<br>Lys Tyr Val Arg Asp Ala Ala Ser Ala Gly Ala Arg Thr Glu Phe Arg<br>    50                      55                    60 | 192 |
| gaa aat gtt tgg gag cgc ctc gcc gag ggt atg gaa ttt gtt cgc ggc<br>Glu Asn Val Trp Glu Arg Leu Ala Glu Gly Met Glu Phe Val Arg Gly<br>65                  70                  75                  80 | 240 |
| aac ttt gat gat gat gca gct ttc gac aac ctc gct gca aca ctc aag<br>Asn Phe Asp Asp Asp Ala Ala Phe Asp Asn Leu Ala Ala Thr Leu Lys<br>                  85                  90                  95 | 288 |
| cgc atc gac aaa acc cgc ggc acc gcc ggc aac tgg gct tac tac ctg<br>Arg Ile Asp Lys Thr Arg Gly Thr Ala Gly Asn Trp Ala Tyr Tyr Leu<br>            100                    105                  110 | 336 |
| tcc att cca cca gat tcc ttc aca gcg gtc tgc cac cag ctg gag cgt<br>Ser Ile Pro Pro Asp Ser Phe Thr Ala Val Cys His Gln Leu Glu Arg<br>        115                    120                  125 | 384 |
| tcc ggc atg gct gaa tcc acc gaa gaa gca tgg cgc cgc gtg atc atc<br>Ser Gly Met Ala Glu Ser Thr Glu Glu Ala Trp Arg Arg Val Ile Ile<br>130                      135                  140 | 432 |
| gag aag cct ttc ggc cac aac ctc gaa tcc gca cac gag ctc aac cag<br>Glu Lys Pro Phe Gly His Asn Leu Glu Ser Ala His Glu Leu Asn Gln<br>145                    150                  155                  160 | 480 |
| ctg gtc aac gca gtc ttc cca gaa tct tct gtg ttc cgc atc gac cac<br>Leu Val Asn Ala Val Phe Pro Glu Ser Ser Val Phe Arg Ile Asp His<br>                165                    170                  175 | 528 |
| tat ttg ggc aag gaa aca gtt caa aac atc ctg gct ctg cgt ttt gct<br>Tyr Leu Gly Lys Glu Thr Val Gln Asn Ile Leu Ala Leu Arg Phe Ala<br>                  180                    185                  190 | 576 |
| aac cag ctg ttt gag cca ctg tgg aac tcc aac tac gtt gac cac gtc<br>Asn Gln Leu Phe Glu Pro Leu Trp Asn Ser Asn Tyr Val Asp His Val<br>                195                    200                  205 | 624 |
| cag atc acc atg act gaa gat att ggc ttg ggt gga cgt gct ggt tac<br>Gln Ile Thr Met Thr Glu Asp Ile Gly Leu Gly Gly Arg Ala Gly Tyr<br>        210                    215                  220 | 672 |
| tac gac ggc atc ggc gca gcc cgc gac gtc atc cag aac cac ctg atc<br>Tyr Asp Gly Ile Gly Ala Ala Arg Asp Val Ile Gln Asn His Leu Ile<br>225                      230                  235                  240 | 720 |
| cag ctc ttg gct ctg gtt gcc atg gaa gaa cca att tct ttc gtg cca<br>Gln Leu Leu Ala Leu Val Ala Met Glu Glu Pro Ile Ser Phe Val Pro<br>                245                    250                  255 | 768 |
| gcg cag ctg cag gca gaa aag atc aag gtg ctc tct gcg aca aag ccg<br>Ala Gln Leu Gln Ala Glu Lys Ile Lys Val Leu Ser Ala Thr Lys Pro<br>            260                    265                  270 | 816 |
| tgc tac cca ttg gat aaa acc tcc gct cgt ggt cag tac gct gcc ggt<br>Cys Tyr Pro Leu Asp Lys Thr Ser Ala Arg Gly Gln Tyr Ala Ala Gly<br>        275                    280                  285 | 864 |
| tgg cag ggc tct gag tta gtc aag gga ctt cgc gaa gaa gat ggc ttc<br>Trp Gln Gly Ser Glu Leu Val Lys Gly Leu Arg Glu Glu Asp Gly Phe<br>290                      295                  300 | 912 |
| aac cct gag tcc acc act gag act ttc gcg gct tgt acc tta gag atc<br>Asn Pro Glu Ser Thr Thr Glu Thr Phe Ala Ala Cys Thr Leu Glu Ile<br>305                    310                  315                  320 | 960 |
| acg tct cgt cgc tgg gct ggt gtg ccg ttc tac ctg cgc acc ggt aag<br>Thr Ser Arg Arg Trp Ala Gly Val Pro Phe Tyr Leu Arg Thr Gly Lys<br>                325                    330                  335 | 1008 |
| cgt ctt ggt cgc cgt gtt act gag att gcc gtg gtg ttt aaa gac gca<br>Arg Leu Gly Arg Arg Val Thr Glu Ile Ala Val Val Phe Lys Asp Ala<br>            340                    345                  350 | 1056 |
| cca cac cag cct ttc gac ggc gac atg act gta tcc ctt ggc caa aac<br>Pro His Gln Pro Phe Asp Gly Asp Met Thr Val Ser Leu Gly Gln Asn<br>        355                    360                  365 | 1104 |

-continued

```
gcc atc gtg att cgc gtg cag cct gat gaa ggt gtg ctc atc cgc ttc      1152
Ala Ile Val Ile Arg Val Gln Pro Asp Glu Gly Val Leu Ile Arg Phe
370                 375                 380 ggt tcc aag gtt cca ggt tct gcc atg gaa gtc cgt gac gtc aac atg      1200
Gly Ser Lys Val Pro Gly Ser Ala Met Glu Val Arg Asp Val Asn Met
385                 390                 395                 400 gac ttc tcc tac tca gaa tcc ttc act gaa gaa tca cct gaa gca tac      1248
Asp Phe Ser Tyr Ser Glu Ser Phe Thr Glu Glu Ser Pro Glu Ala Tyr
                405                 410                 415 gag cgc ctc att ttg gat gcg ctg tta gat gaa tcc agc ctc ttc cct      1296
Glu Arg Leu Ile Leu Asp Ala Leu Leu Asp Glu Ser Ser Leu Phe Pro
            420                 425                 430 acc aac gag gaa gtg gaa ctg agc tgg aag att ctg gat cca att ctt      1344
Thr Asn Glu Glu Val Glu Leu Ser Trp Lys Ile Leu Asp Pro Ile Leu
        435                 440                 445 gaa gca tgg gat gcc gat gga gaa cca gag gat tac cca gcg ggt acg      1392
Glu Ala Trp Asp Ala Asp Gly Glu Pro Glu Asp Tyr Pro Ala Gly Thr
450                 455                 460 tgg ggt cca aag agc gct gat gaa atg ctt tcc cgc aac ggt cac acc      1440
Trp Gly Pro Lys Ser Ala Asp Glu Met Leu Ser Arg Asn Gly His Thr
465                 470                 475                 480 tgg cgc agg cca                                                      1452
Trp Arg Arg Pro
```

<210> SEQ ID NO 12
<211> LENGTH: 484
<212> TYPE: PRT
<213> ORGANISM: Corynebacterium glutamicum

<400> SEQUENCE: 12

```
Met Val Ile Phe Gly Val Thr Gly Asp Leu Ala Arg Lys Lys Leu Leu
 1               5                  10                  15

Pro Ala Ile Tyr Asp Leu Ala Asn Arg Gly Leu Leu Pro Pro Gly Phe
                20                  25                  30

Ser Leu Val Gly Tyr Gly Arg Arg Glu Trp Ser Lys Glu Asp Phe Glu
            35                  40                  45

Lys Tyr Val Arg Asp Ala Ala Ser Ala Gly Ala Arg Thr Glu Phe Arg
        50                  55                  60

Glu Asn Val Trp Glu Arg Leu Ala Glu Gly Met Glu Phe Val Arg Gly
 65                  70                  75                  80

Asn Phe Asp Asp Asp Ala Ala Phe Asp Asn Leu Ala Ala Thr Leu Lys
                85                  90                  95

Arg Ile Asp Lys Thr Arg Gly Thr Ala Gly Asn Trp Ala Tyr Tyr Leu
            100                 105                 110

Ser Ile Pro Pro Asp Ser Phe Thr Ala Val Cys His Gln Leu Glu Arg
        115                 120                 125

Ser Gly Met Ala Glu Ser Thr Glu Glu Ala Trp Arg Arg Val Ile Ile
    130                 135                 140

Glu Lys Pro Phe Gly His Asn Leu Glu Ser Ala His Glu Leu Asn Gln
145                 150                 155                 160

Leu Val Asn Ala Val Phe Pro Glu Ser Ser Val Phe Arg Ile Asp His
                165                 170                 175

Tyr Leu Gly Lys Glu Thr Val Gln Asn Ile Leu Ala Leu Arg Phe Ala
            180                 185                 190

Asn Gln Leu Phe Glu Pro Leu Trp Asn Ser Asn Tyr Val Asp His Val
        195                 200                 205
```

-continued

```
Gln Ile Thr Met Thr Glu Asp Ile Gly Leu Gly Gly Arg Ala Gly Tyr
    210                 215                 220

Tyr Asp Gly Ile Gly Ala Ala Arg Asp Val Ile Gln Asn His Leu Ile
225                 230                 235                 240

Gln Leu Leu Ala Leu Val Ala Met Glu Glu Pro Ile Ser Phe Val Pro
                245                 250                 255

Ala Gln Leu Gln Ala Glu Lys Ile Lys Val Leu Ser Ala Thr Lys Pro
                260                 265                 270

Cys Tyr Pro Leu Asp Lys Thr Ser Ala Arg Gly Gln Tyr Ala Ala Gly
            275                 280                 285

Trp Gln Gly Ser Glu Leu Val Lys Gly Leu Arg Glu Glu Asp Gly Phe
    290                 295                 300

Asn Pro Glu Ser Thr Thr Glu Thr Phe Ala Ala Cys Thr Leu Glu Ile
305                 310                 315                 320

Thr Ser Arg Arg Trp Ala Gly Val Pro Phe Tyr Leu Arg Thr Gly Lys
                325                 330                 335

Arg Leu Gly Arg Arg Val Thr Glu Ile Ala Val Val Phe Lys Asp Ala
                340                 345                 350

Pro His Gln Pro Phe Asp Gly Asp Met Thr Val Ser Leu Gly Gln Asn
            355                 360                 365

Ala Ile Val Ile Arg Val Gln Pro Asp Glu Gly Val Leu Ile Arg Phe
370                 375                 380

Gly Ser Lys Val Pro Gly Ser Ala Met Glu Val Arg Asp Val Asn Met
385                 390                 395                 400

Asp Phe Ser Tyr Ser Glu Ser Phe Thr Glu Glu Ser Pro Glu Ala Tyr
                405                 410                 415

Glu Arg Leu Ile Leu Asp Ala Leu Leu Asp Glu Ser Ser Leu Phe Pro
                420                 425                 430

Thr Asn Glu Glu Val Glu Leu Ser Trp Lys Ile Leu Asp Pro Ile Leu
        435                 440                 445

Glu Ala Trp Asp Ala Asp Gly Glu Pro Glu Asp Tyr Pro Ala Gly Thr
    450                 455                 460

Trp Gly Pro Lys Ser Ala Asp Glu Met Leu Ser Arg Asn Gly His Thr
465                 470                 475                 480

Trp Arg Arg Pro
113
```

GLUCOSE-6-PHOSPHATE DEHYDROGENASE

TECHNICAL FIELD

The present invention relates to a novel glucose-6-phosphate dehydrogenase (hereinafter referred to as "G6PD") derived from a bacterium belonging to the genus *Corynebacterium*, a DNA encoding the enzyme, a recombinant DNA comprising the DNA, a transformant comprising the recombinant DNA, a transformant comprising the DNA on its chromosome, and a process for producing L-amino acid which comprises culturing the transformant.

BACKGROUND ART

In order to obtain a bacterial strain which produces an amino acid efficiently, it is important to know properties of genes relating to the biosynthesis of the amino acid in the bacterium and their style for controlling expression and activity and to carry out rational breeding based thereon.

One of the important methods for understanding the functions of genes relating to the amino acid production is a genetic method, for example, in which a relationship between increase or decrease in amino acid productivity and gene mutation is clarified.

Breeding of amino acid-producing microorganisms is mainly carried out by endowing resistance to drugs such as amino acid analogues and the like, but in many cases, it is not clear which gene provides the productivity improvement by its mutation.

NADPH is necessary as a coenzyme at reduction reaction in the amino acid biosynthesis in many microorganisms. For example, 4 molecules of NADPH are necessary for the biosynthesis of 1 molecule of L-lysine. In the same manner, 3 molecules of NADPH are necessary for 1 molecule of threonine, and 5 molecules of NADPH are necessary for 1 molecule of isoleucine. Thus, two or more molecules of NADPH are necessary for the biosynthesis of 1 molecule of most amino acids. Accordingly, supply of NADPH is an important subject in producing these amino acids using microorganisms.

In many microorganisms, NADPH-supplying enzymes are limited. It is considered that the enzymes which can supply NADPH on the main pathways of sugar metabolism of the microorganisms are mainly G6PD [EC 1.1.1.49] and 6-phosphogluconate dehydrogenase [EC 1.1.1.4] in the pentose phosphate pathway (HMP) and isocitrate dehydrogenase [EC-1.1.1.41] in the TCA pathway.

Particularly, G6PD, which is the first enzyme of HMP and is also the parting point-enzyme from the Embden-Meyerhof pathway (EMP), is considered to be a very important enzyme for the production of various amino acids by bacteria belonging to the genus *Escherichia* and the genus *Corynebacterium*, and various analyses have been carried out mainly on its various biochemical properties. For example, G6PD of bacteria belonging to the genus *Corynebacterium* is described in *Journal of Bacteriology*, 98, 1151 (1969), *Agricultural and Biological Chemistry*, 51, 101 (1987) and Japanese Published Unexamined Patent Application No. 224661/97, but the investigation for productivity improvement of amino acids using the enzyme has not been reported.

Also, the nucleotide sequence of G6PD of bacteria such as *Escherichia coli* and *Corynebacterium glutamicum*, the nucleotide sequence of the gene has been found (*Journal of Bacteriology*, 173, 968 (1991) and Japanese Published Unexamined Patent Application No. 224661/97), but the investigation for productivity improvement of amino acids using the gene has not been reported.

DISCLOSURE OF THE INVENTION

An object of the present invention is to produce L-amino acid industrially advantageously by using G6PD relating to the biosynthesis of the L-amino acid, a DNA encoding the enzyme, a recombinant DNA obtained by inserting the DNA into a vector or a transformant comprising the recombinant DNA to thereby further increase the L-amino acid productivity by a microorganism.

The present inventors have succeeded in isolating a DNA encoding a polypeptide comprising the amino acid sequence represented by SEQ ID NO:2, and found that it can be used in the production of L-amino acid. Also, as a result of intensive studies, the present inventors found that a polypeptide in which Ala at position 213 in the amino acid sequence represented by SEQ ID NO:2 is replaced with an other amino acid and which has the G6PD activity can further improve the productivity of L-amino acid. Thus, the present invention has been accomplished. Specifically, the present invention relates to the following (1) to(23).

(1) A polypeptide which comprises the amino acid sequence represented by SEQ ID NO:2.

(2) A polypeptide which comprises an amino acid sequence in which Ala at position 213 in the amino acid sequence represented by SEQ ID NO:2 is replaced with an other amino acid, and has G6PD activity.

(3) A polypeptide which comprises the amino acid sequence represented by SEQ ID NO:12.

(4) A polypeptide which comprises an amino acid sequence in which one or several amino acids other than the amino acid residue at position 213 in the amino acid sequence of the polypeptide according to (2) are deleted, substituted or added, and has G6PD activity.

(5) A polypeptide which comprises an amino acid sequence in which one or several amino acids other than the amino acid residue at position 213 in the amino acid sequence represented by SEQ ID NO:12 are deleted, substituted or added, and has G6PD activity.

(6) A DNA which encodes the polypeptides according to any one of (1) to (5).

(7) A DNA which comprises the nucleotide sequence represented by SEQ ID NO:1.

(8) A DNA which comprises a nucleotide sequence in which a nucleotide sequence of positions 637 to 639 encoding Ala in the nucleotide sequence represented by SEQ ID NO:1 is replaced with a codon encoding an amino acid other than Ala.

(9) A DNA which comprises the nucleotide sequence represented by SEQ ID NO:11.

(10) A DNA which hybridizes with a DNA comprising the nucleotide sequence represented by SEQ ID NO:1 under stringent conditions, and encodes a polypeptide having glucose-6-phosphate dehydrogenase activity, wherein a nucleotide sequence corresponding to the nucleotide sequence of positions 637 to 639 encoding Ala in the nucleotide sequence represented by SEQ ID NO:1 is replaced with a codon encoding an amino acid other than Ala.

(11) A DNA which hybridizes with a DNA comprising the nucleotide sequence represented by SEQ ID NO:1 under stringent conditions, and encodes a polypeptide having G6PD activity, wherein a nucleotide sequence corresponding to the nucleotide of position 637 in the nucleotide sequence represented by SEQ ID NO:1 is replaced with adenine.

(12) A recombinant DNA which is obtainable by inserting the DNA according to any one of (6) to (11) into a vector.

(13) The recombinant DNA according to (12), wherein the recombinant DNA is replicable in a microorganism belonging to the genus *Escherichia* or the genus *Corynebacterium*.

(14) A plasmid pCRBzwfM comprised in *Escherichia coli* TOP10 (FERM BP-7135).

(15) A transformant which is obtainable by introducing the recombinant DNA or plasmid according to any one of (12) to (14) into a host cell.

(16) The transformant according to (15), wherein the host cell is a microorganism which is capable of producing L-amino acid.

(17) The transformant according to (16), wherein the host cell is a microorganism belonging to the genus *Escherichia* or the genus *Corynebacterium*.

(18) A transformant belonging to the genus *Escherichia* or the genus *Corynebacterium*, which comprises a chromosome into which the DNA according to any one of (6) to (11) is artificially integrated.

(19) The transformant according to (17) or (18), wherein the microorganism belonging to the genus *Corynebacterium* is *Corynebacterium glutamicum*.

(20) A process for producing a polypeptide, which comprises culturing the transformant according to any one of (15) to (19) in a medium to form and accumulate the polypeptide according to any one of (1) to (5) in a culture, and recovering the polypeptide from the culture.

(21) A process for producing L-amino acid, which comprises culturing the transformant according to any one of (16) to (19) in a medium to form and accumulate L-amino acid which is biosynthesized using NADPH in the culture, and recovering the L-amino acid from the culture.

(22) The process for producing L-amino acid according to (21), wherein the L-amino acid which is biosynthesized using NADPH is selected from L-lysine, L-threonine, L-isoleucine, L-tryptophan, L-phenylalanine, L-tyrosine, L-histidine and L-cysteine.

(23) The process for producing L-amino acid according to (21), wherein the L-amino acid is L-lysine.

The present invention is described below in detail.

The polypeptide of the present invention is a polypeptide which comprises the amino acid sequence represented by SEQ ID NO:2 or a polypeptide which comprises an amino acid sequence in which Ala at position 213 of the amino acid sequence represented by SEQ ID NO:2 is substituted with an other amino-acid and has G6PD activity. Examples of the polypeptide include a polypeptide comprising the amino acid sequence represented by SEQ ID NO:12.

A polypeptide which comprises an amino acid sequence in which one or several amino acids in the amino acid sequence comprised in the polypeptide are deleted, substituted or added is also included in the polypeptide of the present invention, so long as it has G6PD activity. However, the polypeptide does not include known G6PD (for example, polypeptide in which Thr at position 120 in SEQ ID NO:2 is replaced with Ala).

The protein which comprises an amino acid sequence in which one or several amino acids are deleted, substituted or added and has G6PD activity can be obtained by introducing a site-directed mutation into a DNA encoding a polypeptide comprising the amino acid sequence represented by SEQ ID NO:2 or 12, using the site-directed mutagenesis described in *Molecular Cloning, A Laboratory Manual*, Second Edition, Cold Spring Harbor Laboratory Press (1989) (hereinafter referred to as "*Molecular Cloning*, Second Edition"), *Current Protocols in Molecular Biology*, John Wiley & Sons (1987–1997) (hereinafter referred to as "*Current Protocols in Molecular Biology*"), *Nucleic Acids Research*, 10, 6487 (1982), *Proc. Natl. acad. Sci. USA*, 79, 6409 (1982), *Gene*, 34, 315 (1985), *Nucleic Acids Research*, 13, 4431 (1985), *Proc. Natl. acad. Sci. USA*, 82, 488 (1985) and the like. It also can be obtained by introducing a site-directed mutation according to the above method into a DNA encoding a polypeptide which originally has a sequence in which one or several amino acids are deleted, substituted or added from the amino acid sequence represented by SEQ ID NO:2 and has the G6PD activity (e.g., a G6PD derived from a microorganism close to *Corynebacterium glutamicum*) to thereby replace an amino acid corresponding to the amino acid at position 213 of the amino acid sequence represented by SEQ ID NO:2 with an other amino acid.

The number of amino acids to be deleted, substituted or added is not particularly limited, but is the number that can be deleted, substituted or added by a well known method such as the site-directed mutagenesis or the like, and is preferably from 1 to 10 and more preferably from 1 to 5.

Also, in order that the polypeptide of the present invention has the G6PD activity, it is preferable that the polypeptide has homology of at least 60% or more, generally 80% or more, particularly 95% or more, with the amino acid sequence described in SEQ ID NO:2 or 12, when calculated using BLAST [*J. Mol. Biol.*, 215, 403 (1990)], FASTA [*Methods in Enzymology*, 183, 63–98 (1990)] or the like.

Examples of the DNA of the present invention encoding the polypeptide of the present invention include a DNA comprising the nucleotide sequence represented by SEQ ID NO:1, a DNA comprising a nucleotide sequence in which a nucleotide sequence of positions 637 to 639 encoding Ala in the nucleotide sequence represented by SEQ ID NO:1 is replaced with a codon encoding an amino acid other than Ala (hereinafter referred to as "SEQ ID NO:1 sub"), and a DNA comprising the nucleotide sequence represented by SEQ ID NO:11 in which the nucleotide at position 637 in the nucleotide sequence SEQ ID NO:1 is adenine.

The DNA of the present invention also includes a DNA which hybridizes with a DNA comprising the nucleotide sequence represented by SEQ ID NO:1 under stringent conditions, has a nucleotide sequence in which a nucleotide sequence of positions 637 to 639 encoding Ala in the nucleotide sequence represented by SEQ ID NO:1 is replaced with a codon encoding an amino acid other than Ala, and encodes a polypeptide having G6PD activity. However, the DNA of the present invention does not include known DNA (e.g., a DNA in which adenine at position 358 in SEQ ID NO:1 is replaced with guanine).

Herein, the DNA which hybridizes with the DNA of SEQ ID NO:1 under stringent conditions means a DNA which is obtainable by colony hybridization, plaque hybridization, Southern blot hybridization or the like using a DNA comprising the nucleotide sequence represented by SEQ ID NO:1 or 11 as a probe, and examples thereof include a DNA which can be identified by carrying out hybridization at 65° C. in the presence of 0.7 to 1.0 mol/l of sodium chloride using a filter on which a colony- or plaque-derived DNA is immobilized, and then washing the filter at 65° C. using 0.1-fold to 2-fold concentration SSC solution (composition of 1-fold concentration SSC contains 150 mmol/l sodium chloride and 15 mmol/l sodium citrate). The hybridization can be carried out according to the method described in, e.g., *Molecular Cloning* Second Edition, *Current Protocols in*

*Molecular Biology* or *DNA Cloning 1: Core Techniques, A Practical Approach*, Second Edition, Oxford University (1995). Examples of the DNA which can be hybridized include a DNA containing a nucleotide sequence having at least 60% or more of identity with the nucleotide sequence represented by SEQ ID NO:1 or 11, preferably a DNA containing a nucleotide sequence having 80% or more of identity, more preferably a DNA containing a nucleotide sequence having 95% or more of identity, when calculated using the BLAST, FASTA or the like.

The DNA of the present invention can be obtained from *Corynebacterium glutamicum* No. 58 (FERM BP-7134) or from a mutant having increased L-amino acid productivity obtained by applying a general mutagenizing operation to the strain.

Examples of the mutagenizing operation include the conventional method using N-methyl-N'-nitro-N-nitrosoguanidine (NTG); (*Microbial Experimentation Manual*, 1986, p. 131, Kodansha Scientific).

The DNA of the present invention can be isolated by the following method.

That is, a chromosomal DNA is prepared from a strain containing the DNA by, e.g., the method of Saito et al. [*Biochimica et Biophysica Acta*, 72, 619 (1963)], and the chromosomal DNA is digested with an appropriate restriction enzyme. The obtained DNA fragment is ligated with a vector (e.g., plasmid) which is autonomously replicable in bacterial cells, and the ligated DNA is introduced into a microorganism which is defective in the G6PD activity. A transformant is isolated from the obtained microorganism using the G6PD activity as the index, and the gene for the enzyme is isolated from the transformant.

For example, a strain of *Escherichia coli* which is defective in only glucose-6-phosphate isomerase can grow in a medium containing glucose as the sole carbon source, but a strain further defective in G6PD cannot grow in a medium containing glucose as the sole carbon source [*Escherichia coli* and *Salmonella typhimurium*, 192 (1996)]. Thus, the DNA of the present invention can be isolated from the strain by selecting a strain which became able to grow in a medium containing glucose as the sole carbon source from the strains obtained by introducing the DNA into the double-defective strain.

The microorganism into which the DNA of the present invention is introduced may be a bacterium belonging to any genus, so long as the DNA can be expressed. Also, the autonomously replicable vector may be any vector, so long as it can autonomously replicate in the bacterium. For example, when a microorganism belonging to the genus *Escherichia*, particularly *Escherichia coli*, is used, the autonomously replicable vector include pUC18 (manufactured by Takara Shuzo) and pBluescript SK(−) (manufactured by TOYOBO). Also, it may be a shuttle vector which is autonomously replicable in both *Escherichia coil* and a bacterium of the genus *Corynebacterium*, such as pCE54 (Japanese Published Unexamined Patent Application No. 105999/83).

The vector can be ligated with the DNA of the present invention by a general method using T4 DNA ligase and the like. For example, when *Escherichia coli* is used, the vector can be introduced into a host by the method of Hanahan et al. [*Journal of Molecular Biology*, 166, 557 (1983)] and the like.

Also, the gene can also be isolated from a strain which is obtained by synthesizing an oligomer DNA based on the nucleotide sequence information of the G6PD gene (e.g., GenBank accession No. E13655 or the nucleotide sequence represented by SEQ ID NO:1 in the case of *Corynebacterium glutamicum*), carrying out polymerase chain reaction (PCR) using the oligomer DNA as a primer and chromosomal DNA of a microorganism belonging to the genus *Corynebacterium* as the template, ligating the obtained DNA fragment to a vector having a selection marker gene and then introducing it into an appropriate host such as a bacterium of the genus *Escherichia* or the genus *Corynebacterium*. In this case, it is not necessary to use a G6PD defective strain.

In addition, the gene can also be synthesized using a generally used DNA synthesizer, such as ABI 3948 manufactured by Perkin-Elmer, based on a nucleotide sequence of the gene, for example, the nucleotide sequence represented by SEQ ID NO:1.

The DNA of the present invention isolated by the above method is introduced into an expression vector which can replicate and express in a host microorganism, and the host microorganism is transformed with the recombinant vector thus obtained.

The recombinant DNA comprising the DNA encoding the polypeptide of the present invention is preferably a vector which can autonomously replicate and which comprises a promoter, a ribosome binding sequence, the DNA of the present invention and a transcription termination sequence. A gene for regulating the promoter may also be contained in the recombinant DNA.

When a microorganism belonging to the genus *Escherichia* is used, examples of the vector for this object include pBTrp2, pBTac1 and pBTac2 (all available from Boehringer Manhein), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 [*Agric. Biol. Chem.*, 48, 669 (1984)], pLSA1 [*Agric. Biol. Chem.*, 53, 277 (1989)], pGEL1 [*Proc. Natl. Acad Sci.* USA, 82, 4306 (1985)], pBluescript II SK(−) (manufactured by Stratagene), pTrs30 [prepared from *Escherichia coli* JM109/pTrS30 (FERM BP-5407)], PTrs32 [prepared from *Escherichia coli* JM109/pTrS32 (FERM-BP-5408], pGHA2 [prepared from *Escherichia coli* IGH2 (FERM BP-400), Japanese Published Unexamined Patent Application No. 221091/85], pGKA2 [prepared from *Escherichia coli* IGKA2 (FERM BP-6798), Japanese Published Unexamined Patent Application No. 221091/85], pTerm2 (U.S. Pat. No. 4,686,191, U.S. Pat. No. 4,939,094, U.S. Pat. No. 5,160,735), pSupex, pUB110, pTP5, pC194, pEG400 [*J. Bacteriol.*, 172, 2392 (1990)], pGEX (manufactured by Pharmacia) and pET system (manufactured by Novagen). When a microorganism belonging to the genus *Corynebacterium* is used, examples include pCG1 (Japanese Published Unexamined Patent Application No. 134500/82), pCG2 (Japanese Published Unexamined Patent Application No. 35197/83), pCG4 (Japanese Published Unexamined Patent Application No. 183799/82), pCG11 (Japanese Published Unexamined Patent Application No. 134500/82), pCG116, pCE54 and pCB101 (all Japanese Published Unexamined Patent Application no. 105999/83), pCE51, pCE52 and pCE53 [all *Molecular and General Genetics*, 196, 175 (1984)] and pCS299P described in Examples of the present application.

Any promoter can be used, so long as it can function in the host cell. Examples include promoters derived from *Escherichia coli*, phage and the like, such as trp promoter ($P_{trp}$), lac promoter, $P_L$ promoter, $P_R$ promoter, T7 promoter, and the like. Also, artificially designed and modified promoters, such as a promoter in which two $P_{trp}$ are linked in tandem ($P_{trp} \times 2$), tac promoter, lacT7 promoter, letI promoter and the like, can be used.

It is preferred to use a plasmid in which the space between Shine-Dalgarno sequence, which is the ribosome binding sequence, and the initiation codon is adjusted to an appropriate distance (for example, 6 to 18 bases).

In the recombinant DNA of the present invention, the transcription termination sequence is not always necessary for the expression of the DNA of the present invention. However, it is preferred to provide a transcription terminating sequence just downstream of the structural gene.

Any host cell may be used, so long as it is a cell capable of producing L-amino acid described below. Preferably, a microorganism capable of producing the amino acid is used. The microorganism is more preferably a microorganism belonging to the genus *Escherichia* or the genus *Corynebacterium*, still more preferably a microorganism belonging to the genus *Corynebacterium*, and most preferably *Corynebacterium glutamicum*.

Examples of the microorganism include microorganisms belonging to the genus *Serratia*, the genus *Corynebacterium*, the genus *Arthrobacter*, the genus *Microbacterium*, the genus *Bacillus* and the genus *Escherichia*. Specific examples include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* GI698, *Escherichia coli* TB1, *Escherichia coli* ATCC 9637, *Escherichia coli* FERM BP-5985, *Serratia ficaria*, *Serratia fonticola*, *Serratia liquefaciens*, *Serratia marcescens*, *Bacillus subtilis*, *Bacillus amyloliquefacines*, *Corynebacterium ammoniagenes* ATCC 6872, *Brevibacterium immariophilium* ATCC 14068, *Brevibacterium saccharolyticum* ATCC 14066, *Brevibacterium roseum* ATCC 13825, *Brevibacterium thiogenitalis* ATCC 19240, *Corynebacterium glutamicum* ATCC 14067, *Corynebacterium glutamicum* ATCC 13869, *Corynebacterium glutamicum* ATCC 13032, *Corynebacterium glutamicum* ATCC 13869, *Corynebacterium glutamicum* ATCC 13870, *Corynebacterium callunae* ATCC 15991, *Corynebacterium acetoglutamicum* ATCC 15806, *Microbacterium ammoniaphilum* ATCC 15354 and *Corynebacterium thermoaminogenes* AJ 12340. The following microorganism strain or a mutant strain producing L-amino acid derived from the following microorganism strain is preferably used:

*Corynebacterium glutamicum* ATCC 13032;
*Corynebacterium glutamicum* ATCC 13869; and
*Corynebacterium glutamicum* ATCC 13870.

As the recombinant vector introducing-method, any method of introducing a DNA into the host cell can be used. For example, when a microorganism belonging to the genus *Escherichia* is used, examples include the method which comprises the use of a calcium ion [*Proc. Natl. Acad. Sci. USA*, 69, 2110 (1972)] and the electroporation method [*Methods in Enzymology*, 235, 375 (1994)]. When a microorganism belonging to the genus *Corynebacterium* is used, examples include the protoplast method (e.g., Japanese Published Unexamined Patent Application No. 186492/82 and Japanese Published Unexamined Patent Application No. 18649/82), and the electroporation method [e.g., *Journal of Bacteriology*, 175, 4096 (1993)].

The microorganism belonging to the genus *Escherichia* or the genus *Corynebacterium* and comprising the DNA of the present invention on the chromosome may be any microorganism in which the DNA fragment is artificially integrated into the chromosome by a genetic recombination or a mutagenizing treatment. For example, it may be a strain modified by a mutagenizing treatment from a strain containing a G6PD gene of any sequence into a strain comprising the DNA of the present invention, or a strain in which the DNA fragment is artificially integrated into the chromosome by the homologous recombination method [*Bio/Technology*, 9, 84 (1991); *Microbiology*, 144, 1863 (1998)], the method which uses a phage or transposon [*Escherichia coli* and *Salmonella typhimurium*, 2325–2339 (1996)] and the like. Preferably, a strain in which the DNA is integrated into the chromosome by the homologous recombination method is exemplified.

In the present invention, a strain obtained by a mutagenizing treatment as well as a strain obtained by a genetic recombination is also called a transformant.

The polypeptide of the present invention can be produced by culturing the transformant of the present invention thus obtained in a medium to thereby form and accumulate the polypeptide of the present invention in the culture, and then recovering it from the culture.

Also, L-amino acid can be produced by culturing the transformant in a medium to thereby form and accumulate the L-amino acid in the culture, and then recovering it from the culture.

As the L-amino acid, any amino acid can be produced, so long as it needs NADHP for its biosynthesis. Examples include L-lysine, L-threonine, L-isoleucine, L-tryptophan, L-phenylalanine, L-tyrosine, L-histidine and L-cysteine. Also, a compound other than amino acids which uses these amino acids as intermediates can be produced. Preferably, L-lysine is exemplified. Biosynthetic pathways of amino acids are shown in FIG. 1. In the drawing, reactions which consume NADPH are shown with an underline.

The transformant of the present invention can be cultured in a medium according to the usual method used for culturing a host.

As a medium used for culturing, the general nutritional medium containing a carbon source, a nitrogen source, inorganic salts and the like can be used.

Any carbon source which can be assimilated by the transformant or the microorganism of the present invention is used. Examples include carbohydrates such as glucose, fructose, sucrose, molasses containing them, starch, starch hydrolysate, etc.; organic acids such as acetic acid, propionic acid, etc.; and alcohols such as ethanol, propanol, etc.

Examples of the nitrogen source include ammonia; ammonium salts of inorganic acids or organic acids such as ammonium chloride, ammonium sulfate, ammonium acetate, ammonium phosphate, etc.; other nitrogen-containing compounds; peptone; meat extract; yeast extract; corn steep liquor; casein hydrolysate; soybean meal and soybean meal hydrolysate; and various cells obtained by fermentation and their digested products.

Examples of the inorganic salts include potassium dihydrogen phosphate, dipotassium : hydrogen phosphate, magnesium phosphate, magnesium sulfate, sodium chloride, ferrous sulfate, manganese sulfate, copper sulfate and calcium carbonate.

Culturing is carried out under aerobic conditions by shaking culture, submerged spinner culture under aeration or the like. The culturing temperature is preferably from 15 to 40° C., and the culturing time is generally from 16 hours to 7 days. The pH during the culturing is preferably maintained at 3.0 to 9.0. The pH can be adjusted using an inorganic or organic acid, an alkali solution, urea, calcium carbonate, ammonia or the like.

Also, antibiotics such as ampicillin, tetracycline, and the like can be added to the medium during culturing, if necessary.

When a microorganism transformed with a recombinant vector harboring an inducible promoter as the promoter is cultured, an inducer may be added to the medium, if necessary. For example, when a microorganism transformed with a recombinant vector harboring lac promoter is cultured, isopropyl-β-D-thiogalactopyranoside (IPTG) or the like may be added to the medium, or when a microorganism transformed with a recombinant vector harboring trp promoter is cultured, indoleacrylic acid or the like may be added to the medium.

After culturing, precipitates such as cells and the like are removed from the culture, and L-amino acid can be recovered from the culture using ion exchange treatment, concentration, salting out and the like in combination.

The polypeptide produced by the transformant of the present invention can be isolated and purified using the usual method for isolating and purifying an enzyme. For example, when the polypeptide of the present invention is expressed as a soluble product in the host cells, the cells are recovered by centrifugation after culturing, suspended in an aqueous buffer, and are disrupted using an altrasonicator, a French press, a Manton Gaulin homogenizer, a Dynomill or the like to obtain a cell-free extract solution. From the supernatant obtained by centrifuging the cell-free extract solution, a purified product can be obtained by the usual method used for isolating and purifying an enzyme, for example, solvent extraction; salting out using ammonium sulfate or the like; desalting; precipitation using an organic solvent; anion exchange chromatography using a resin, such as diethylaminoethyl (DEAE)-Sepharose, DIAION HPA-75 (manufactured by Mitsubishi Chemical) etc.; cation exchange chromatography using a resin, such as S-Sepharose FF (manufactured by Pharmacia) etc.; hydrophobic chromatography using a resin, such as butyl sepharose, phenyl sepharose etc.; gel filtration using a molecular sieve; affinity chromatography, chromatofocusing; electrophoresis, such as isoelectronic focusing etc.; and the like alone or in combination thereof.

When the polypeptide is expressed as an inclusion body intracellularly, the cells are recovered in the same manner, disrupted and centrifuged to recover the polypeptide as the precipitate fraction. The inclusion body of the recovered polypeptide is solubilized with a protein denaturing agent. The solubilized polypeptide solution is diluted or dialyzed to lower the concentration of the protein denaturing agent in the solution to thereby restore the normal tertiary structure of the polypeptide. After the procedure, a purified product of the polypeptide can be obtained by a purification/isolation method similar to the above.

When the polypeptide of the present invention is secreted extracellularly, the polypeptide can be recovered in the culture supernatant. Specifically, the culture supernatant is obtained by treating the culture in a treatment similar to the above, such as centrifugation or the like. Then, a purified product can be obtained from the supernatant using a purification/isolation method similar to the above.

Examples of the polypeptide thus obtained include a polypeptide comprising the amino acid sequence represented by SEQ ID NO:2 or 12.

Also, the polypeptide of the present invention can be produced by a chemical synthesis method, such as Fmoc (fluorenylmethyloxycarbonyl) method, tBoc (t-butyloxycarbonyl) method or the like. Furthermore, it can be chemically synthesized using a peptide synthesizer manufactured by Advanced ChemTech, Perkin-Elmer, Pharmacia, Protein Technology Instrument, Synthecell-Vega, PerSeptive, Shimadzu Corporation or the like.

Examples of the present invention are shown below; however, the present invention is not limited to these Examples.

Figure 1:
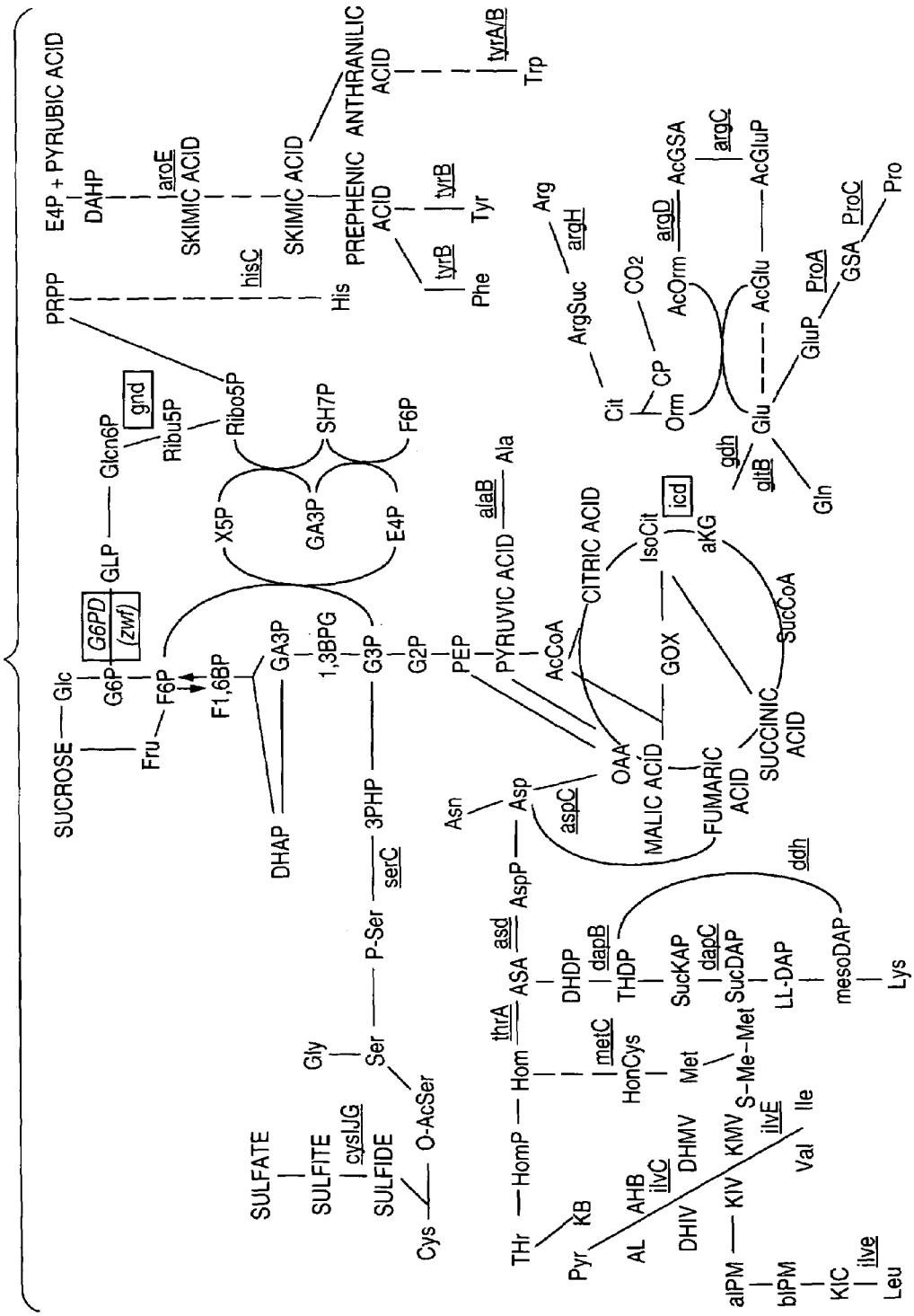
FIG. 1 shows biosynthetic pathways of 20 amino acids constituting proteins in a bacterium of the genus *Corynebacterium*. The underlined parts show reactions which consume NADPH. The framed parts show reactions which produce NADPH.

The genes which correspond to enzymes relating to respective reactions are named basically by the nomenclature of *Escherichia coil*. In the drawing, glucose-6-phosphate dehydrogenase is represented by G6PD(zwf).

Figure 2:
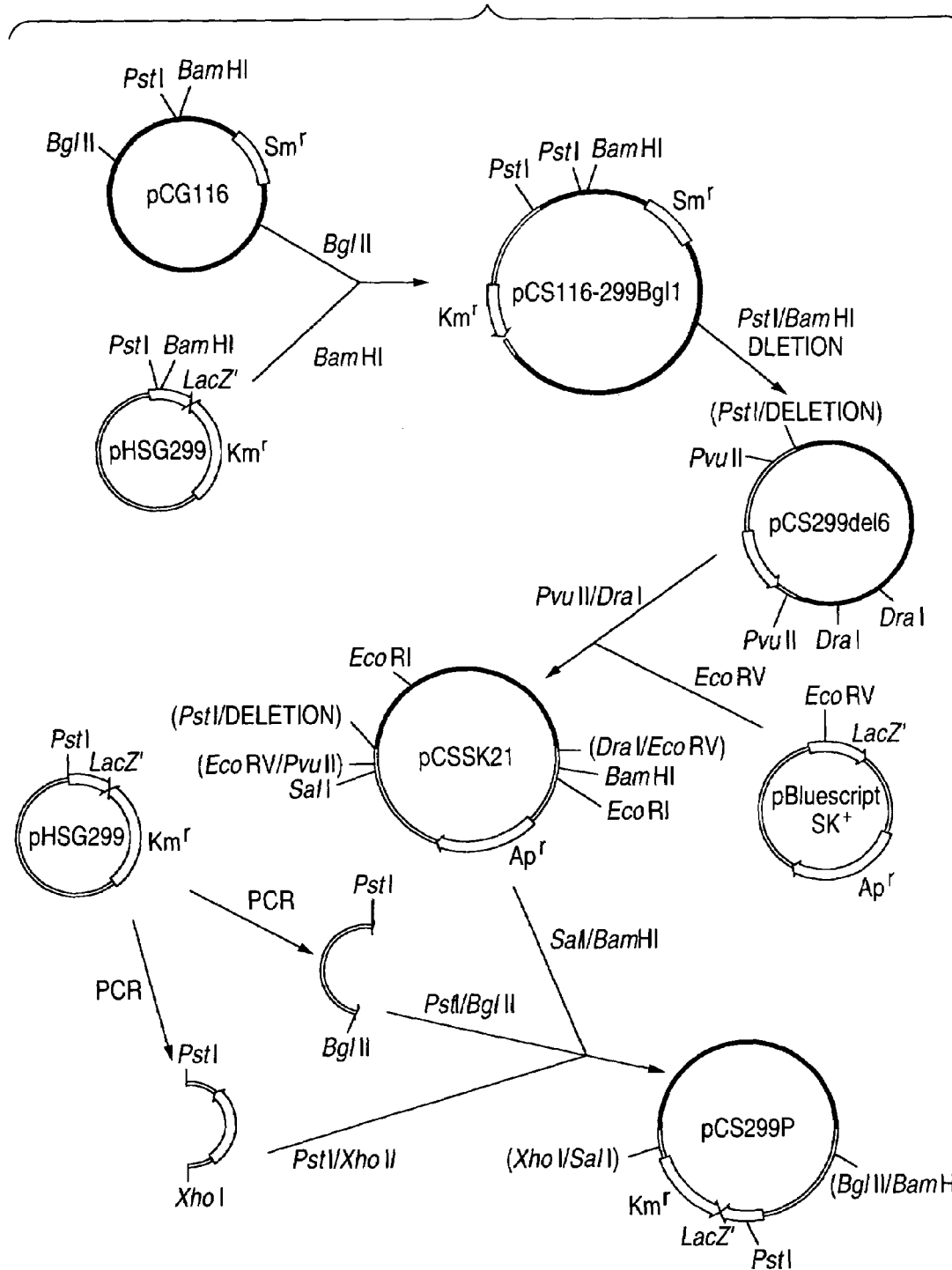

FIG. 2 shows construction steps of pCS299P.

BEST MODE FOR CARRYING OUT THE INVENTION

EXAMPLE 1

Preparation of Novel G6PD Gene (1) Determination of G6PD Gene Nucleotide Sequence

*Corynebacterium glutamicum* No. 58 (hereinafter referred to as "No. 58 strain") is an L-lysine producing strain obtained by applying a mutagenizing operation to *Corynebacterium glutamicum* ATCC 13032 (hereinafter referred to as "ATCC 13032 strain").

The strain has been deposited on Apr. 14, 2000, in International Patent Organism Depositary, National Institute of Advanced Industrial Science and Technology, AIST Tsukuba Central 6, 1-1, Higashi 1-Chome Tsukuba-shi, Ibaraki-ken, Japan (the old name: National Institute of Bioscience and Human technology, Agency of Industrial Science and Technology: 1–3, Higashi 1-chome, Tsukuba-shi, Ibaraki-ken, Japan) with accession number FERM BP-7134 under the Budapest Treaty. G6PD gene of the ATCC 13032 strain and No. 58 strain were cloned as follows.

A chromosomal DNA was prepared from each strain by the method of Saito et al. [*Biochimica et Biophysica Acta*, 72, 619 (1963)]. Also, based on the G6PD gene nucleotide sequence already known in *Corynebacterium glutamicum* MJ233 (GenBank accession number E13655), PCR primers for the target nucleotide sequence were prepared by the usual method. Nucleotide sequences of the primers are shown in SEQ ID NOs:3 and 4. PCR was carried out by 25 cycles, one cycle consisting of a reaction at 94° C. for 1 minute, reaction at 60° C. for 1 minute and reaction at 74° C. for 2 minutes, using a thermal cycler manufactured by Perkin-Elmer (GeneAmp PCR System 9600), Pfu turbo DNA polymerase (manufactured by Stratagene), 100 ng of each chromosomal DNA and the attached-buffer. An amplified PCR product of about 2.2 kb was subjected to agarose gel electrophoresis and extracted and purified using QIAquick Gel Extraction Kit (manufactured by Quiagen).

The above 2.2 kb DNA fragment containing the G6PD gene and a pCR-Blunt vector (manufactured by Invitrogen) were ligated using T4 DNA ligase (manufactured by Takara Shuzo), which was used to transform *Escherichia coli* One Shot TOP10 competent cells (manufactured by Invitrogen) according to the usual method. Each of the transformants selected on an LB agar medium [medium containing 5 g of Yeast Extract (manufactured by Difco), 10 g of Bacto-tryptone (manufactured by Difco), 10 g of sodium chloride and 16 g of agar (manufactured by Ditco) in 1 liter of water and adjusted to pH 7.2] containing 50 µg/ml kanamycin was cultured overnight in LB medium containing 50 µg/ml kanamycin, and plasmids were prepared from the respective culture media thus obtained by the alkaline SDS method (*Molecular Cloning*, Second Edition).

A plasmid containing the G6PD gene derived from the ATCC 13032 strain was named pCRBzwf1, and a plasmid containing the G6PD gene derived from the No. 58 strain was named pCRBzwf2.

Next, nucleotide sequences of G6PD gene on the plasmids were determined by the conventional method. AS a result, it was found that the nucleotide sequences of G6PD genes obtained from the ATCC 13032 strain and the No. 58 strain were completely the same. The nucleotide sequence is shown in SEQ ID NO:1. That is, it was shown that the G6PD gene of the L-lysine producing strain No. 58 is a wild-type one.

(2) Preparation of Novel G6PD Gene

No. 58 strain was subjected to a mutagenizing treatment with NTG (Microbial Experimentation Manual, 1986, p. 131, Kodansha Scientific) and then inoculated onto a minimal agar medium [a medium containing 10 g of glucose, 4 g of ammonium chloride, 2 g of urea, 1 g of potassium dihydrogenphosphate, 3 g of dipotassium hydrogenphosphate, 4 mg of ferrous sulfate heptahydrate, 40 µg of zinc chloride heptahydrate, 200 µg of ferric chloride hexahydrate, 10 µg of copper chloride dihydrate, 10 µg of manganese chloride tetrahydrate, 10 µg of sodium tetraborate decahydrate, 10 µg of ammonium molybdate tetrahydrate, 50 µg of biotin, 5 mg of nicotinic acid and 16 g of agar (manufactured by Difco) in 1 liter of water and adjusted to pH 7.2] containing 1 mg/ml 6-azauracil and cultured at 30° C. for 2 days. The thus formed colonies were isolated and subjected to the L-lysine production test described in Example 2(4) below, clones having higher productivity than that of No. 58 strain were selected. Among these, one strain was named M1 strain. G6PD gene of M1 strain was isolated by the method of (1), and the gene was inserted into the pCR-Blunt vector. The thus obtained recombinant plasmid was named pCR-BzwfM. When its nucleotide sequence was determined, the nucleotide at position 637 of SEQ ID NO:1, which is guanine in the G6PD genes of the ATCC 13032 strain and No. 58 strain, was changed to adenine in the G6PD gene of M1 strain. The nucleotide sequence is shown in SEQ ID NO:11.

As a result of the mutation, Ala at position 213 (codon GCT) from the amino terminal side of the G6PD in the ATCC 13032 strain and No. 58 strain was changed to Thr (codon ACT) in the G6PD in the M1 strain. The amino acid sequence was shown in SEQ ID NO:12.

That is, it was shown that an amino acid substitution mutation of Ala213Thr is present in the G6PD of the M1 Strain. *Escherichia coli* TOP10 comprising the pCRBzwfM has been deposited on Apr. 14, 2000, in International Patent Organism Depositary, National Institute of Advanced Science and Technology, AIST Tsukuba Central 6, 1-1, Higashi 1-Chome Tsukuba-shi, Ibaraki-ken, Japan (the old name: National Institute of Bioscience and Human technology, Agency of Industrial Science and Technology: 1–3, Higashi 1-chome, Tsukuba-shi, Ibaraki-ken, Japan) with accession number FERM BP-7135 under the Budapest Treaty.

EXAMPLE 2

Effect of the Novel G6PD Gene L-Lysine Production (1) Construction of Vector for Gene Substitution In order to examine the effect of amino acid substitution mutation in G6PD shown in Example 1, the G6PD gene of No. 58 strain was substituted into a mutant.

A vector for gene substitution for this substitution was constructed as follows.

Single-stranded 37 mer DNA of and 29 mer DNA comprising the nucleotide sequences represented by SEQ ID NOs:5 and 6, respectively, were synthesized according to the conventional method. They were mixed in 50 µl of 0.1 M NaCl to give a respective concentration of 10 pmole/µl, and allowed to stand at 95° C. for 2 minutes and then at 65° C. for 15 minutes. After cooling to 30° C. over 3 hours, both of the single-stranded DNA molecules were paired to obtain a double-stranded DNA.

pHSG299 (manufactured by Takara Shuzo) was digested with EcoRI and SphI (both manufactured by Takara Shuzo), subjected to agarose gel electrophoresis and then extracted and purified using QIAquick Gel Extraction Kit (manufactured by Quiagen). The thus obtained pHSG299 fragment was ligated with the above double-stranded DNA fragment by using Ligation Kit ver. 2 (manufactured by Takara Shuzo), and *Escherichia coli* DH5α was transformed therewith according to the conventional method. The strain was cultured on LB agar medium containing 50 µg/ml kanamycin, and transformants were selected. Among the transformants, one strain was cultured overnight in LB medium containing 50 µg/ml kanamycin, and a plasmid was prepared from the culture medium thus obtained by the alkaline SDS method. The thus obtained plasmid was named pHSG299L.

(2) Construction of Plasmid pCS299P

A shuttle vector pCS299P which is autonomously replicable in both *Escherichia coli* and a coryneform bacterium was prepared by the following method.

A BglII-digested fragment was obtained by digesting pCG116 [*Bio/Technology*, 11, 921 (1993)] with BglII (manufactured by Takara Shuzo).

After digesting pHSG299 (manufactured by Takara Shuzo) with BamHI (manufactured by Takara Shuzo), the thus obtained BamHI-digested fragment was concentrated by ethanol precipitation according to the conventional method, and the fragment was treated with alkaline phosphatase. The two fragments thus obtained were mixed and subjected to a ligation reaction by using Ligation Kit. ver. 1 (manufactured by Takara Shuzo). Using the reaction product, *Escherichia coli* NM522 was transformed according to the conventional method (*Molecular Cloning*, Second Edition). The strain was cultured on LB agar medium containing 20 µg/ml kanamycin to select a transformant. The transformant was cultured overnight in LB agar medium containing 20 µg/ml kanamycin, and a plasmid was prepared from the culture thus obtained by the alkaline SDS method to obtain pCS116-299Bgl1 DNA.

Restriction sites of the pCS116-299Bgl1 DNA were confirmed according to the conventional method.

Using the pCS116-299Bgl1 DNA, *Corynebacterium ammoniagenes* ATCC 6872 was transformed by electroporation [*FEMS Microbiology Letters*, 65, 299 (1989)].

A transformant was selected by culturing the strain on a CM agar medium [a medium containing 10 g of Polypeptone S (manufactured by Nihon Pharmaceutical), 5 g of Yeast extract S (manufactured by Nihon Pharmaceutical), 10 g of Ehrlich meat extract (manufactured by Kyokuto Pharmaceutical), 3 g of sodium chloride and 30 μg of biotin in 1 liter of water and adjusted to pH 7.2] containing 20 μg/ml kanamycin. A plasmid was extracted from the transformant according to the conventional method, and the plasmid was digested with restriction enzymes to confirm that the plasmid is pCS116-299Bgl1.

The pCS116-299Bgl1 DNA was digested with PstI (manufactured by Takara Shuzo) and BamHI and then purified by ethanol precipitation. A partially deleted plasmid was prepared from the thus obtained DNA using a deletion kit for kilo-sequencing (manufactured by Takara Shuzo). *Escherichia coli* NM522 was transformed using the plasmid according to the conventional method. The strain was cultured on LB agar medium containing 20 μg/ml kanamycin to select transformants. The transformants were cultured overnight in LB medium containing 20 μg/ml kanamycin, and plasmids were prepared from the culture medium thus obtained by the alkaline SDS method. According to the conventional method, a restriction map of each of the thus obtained plasmids was prepared, and plasmids having a different partially-deleted length were selected.

*Corynebacterium ammoniagenes* ATCC 6872 was transformed using the plasmids by electroporation thus selected. The transformants thus obtained were spread on CM agar medium containing 20 μg/ml kanamycin and cultured at 30° C. for 2 days, and plasmids which was autonomously replicable in *Corynebacterium ammoniagenes* were selected based on whether kanamycin resistant colonies were formed or not.

Among the plasmids having autonomous replication ability, a plasmid having the longest deletion region was selected, and this plasmid was named pCS299del6.

The pCS299del6 DNA was prepared from the transformant according to the conventional method and then digested with restriction enzymes DraI and PvuII (both manufactured by Takara Shuzo). The digested DNA fragments were fractionated by agarose gel electrophoresis, and about 2.7 kb DNA fragment having a pCG116-derived DNA was separated and then extracted and purified by using DNA prep (manufactured by Asahi Glass).

The DNA of pBluescript SK(+) (manufactured by TOYOBO) was digested with EcoRV (manufactured by Takara Shuzo) according to the conventional method. The thus digested DNA fragments were concentrated by ethanol precipitation and then subjected to alkaline phosphatase treatment. The treated DNA fragments were fractionated by agarose gel electrophoresis and then extracted and purified using the DNA prep.

The 2.7 kb DNA fragment and pBluescript SK(+) fragment were ligated using the Ligation Kit ver. 1, and then the *Escherichia coli* NM522 was transformed by using the ligated DNA according to the conventional method. The strain was cultured on LB agar medium containing 100 μg/ml ampicillin, 50 μg/ml X-Gal (5-bromo-4-chloro-3-indoyl-β-D-galactoside) and 1 mmol/l IPTG (isopropylthio-β-D-galactoside) to select transformants. The transformants were cultured overnight in LB medium containing 100 μg/ml ampicillin, and plasmids were prepared from the culture thus obtained by the alkaline SDS method. According to the conventional method, a restriction map of each of the thus obtained plasmids was prepared. A plasmid capable of forming 3.4 kb DNA fragment and 2 kb DNA fragment by EcoRI digestion was named pCSSK21.

DNA fragments having the nucleotide sequences represented by SEQ ID NOs:7 and 8 were synthesized, and PCR was carried out by using the DNA fragments as primers, and the pHSG299 DNA as the template, and using Taq DNA polymerase (manufactured by Takara Shuzo) according to the reaction conditions attached thereto. The reaction product was precipitated with ethanol according to the conventional method and then digested with restriction enzymes PstI and XhoI (manufactured by Takara Shuzo). The digested DNA fragments were fractionated by agarose gel electrophoresis, and the about 1.3 kb DNA fragment thus obtained was extracted and purified using the DNA prep.

DNA fragments having the nucleotide sequences represented by SEQ ID NOs:9 and 10 were synthesized, and PCR was carried out by using the Taq DNA polymerase according to the reaction conditions attached thereto, wherein the DNA fragments were used as primers, and the pHSG299 DNA was used as the template. The reaction product was precipitated with ethanol according to the conventional method and then digested with restriction enzymes PstI and BglII. The digested DNA fragments were fractionated by agarose gel electrophoresis, and the about 1.3 kb DNA fragment thus obtained was extracted and purified using the DNA prep.

The plasmid pCSSK21 thus obtained was digested with SalI (manufactured by Takara Shuzo) and BamHI. The digested DNA fragments were fractionated by agarose gel electrophoresis, and the about 2.7 kb DNA fragment thus obtained was extracted and purified by using the DNA prep. The three DNA fragments extracted and purified above were mixed and then ligated by using the Ligation Kit ver. 1.

The *Escherichia coli* NM522 was transformed with the ligated DNA fragment according to the conventional method. The strain was cultured on LB agar medium containing 20 μg/ml kanamycin, 50 μg/ml X-Gal and 1 mmol/l IPTG to select transformants.

The transformants were cultured overnight in LB medium containing 20 μg/ml kanamycin, and plasmids were prepared from the culture medium thus obtained by the alkaline SDS method. According to the conventional method, a restriction map of each of the thus obtained plasmids was prepared, and the plasmid having the structure described in FIG. 1 was named pCS299P.

The plasmids pCS299P and pHSG299L were digested with XbaI and PstI (both manufactured by Takara Shuzo) and then subjected to agarose gel electrophoresis. Each of the 2.5 kb fragment containing a pCS299P-derived replication initiation region (Oric) in bacteria of the genus *Corynebacterium* and the pHSG299L fragment was extracted and purified by using QIAquick Gel Extraction Kit (manufactured by QUIAGEN). The 2.5 kb DNA fragment and the pHSG299L fragment were ligated by using Ligation Kit ver. 2 (manufactured by Takara Shuzo) and used to transform into *Escherichia coli* DHα according to the conventional method. A plasmid was prepared from the thus obtained transformant in the same manner as the method. The thus obtained plasmid was named pHSG299OC.

Plasmids pMOB3 (ATCC 77282) and pHSG299OC were digested with PstI (manufactured by Takara Shuzo) and then subjected to agarose gel electrophoresis. Each of the 2.6 kb fragment containing a pMOB3-derived *Bacillus subtilis* levan sucrase (SacB) gene and the pHSG299OC fragment was extracted and purified by using QIAquick Gel Extraction Kit (manufactured by QUIAGEN).

The 2.6 kb DNA fragment and the pHSG299OC fragment were ligated by using Ligation Kit ver. 2 (manufactured by Takara Shuzo) and transformed into *Escherichia coli* DHα according to the conventional method. The strain was cultured on LB agar medium containing 50 μg/ml kanamycin to select a transformant. A plasmid was prepared from the thus obtained transformant in the same manner as the above method. The plasmid was named pHSG299OCSB.

A 5.1 kb DNA fragment obtained by digesting the pHSG299OCSB with NotI was subjected to agarose gel electrophoresis and then extracted and purified by using QIAquick Gel Extraction Kit (manufactured by QUIAGEN). pCRBzwfM prepared in Example 1 was digested with NotI, subjected to agarose gel electrophoresis and then extracted and purified by using QIAquick Gel Extraction Kit (manufactured by QUIAGEN). A NotI fragment containing Oric and SacB gene was connected to the NotI site of pCRBzwfM by using Ligation Kit ver. 2 (manufactured by Takara Shuzo) and transformed into *Escherichia coli* DH5α according to the conventional method. The strain was cultured on LB agar medium containing 50 μg/ml kanamycin to select a transformant. A plasmid was prepared from the thus obtained transformant in the same manner as the above method. The plasmid was named pCRBOSzwfM and used as a recombinant vector for G6PD gene.

(3) Substitution of G6PD Gene of No. 58 Strain

The pCRBOSzwfM containing mutant G6PD gene was introduced into the No. 58 strain and then integrated into chromosomal DNA by homologous recombination using the method of Ikeda et al. [*Microbiology*, 144, 1863 (1998)].

Strains in which second homologous recombination was occurred were selected by the selection method which uses a property of the *Bacillus subtilis* levan sucrase encoded by pCRBOSzwfM to produce a suicide substrate [*Journal of Bacteriology*, 174, 5462 (1992)], and a strain in which the G6PD gene (wild-type) originally contained in the No. 58 strain was substituted with the mutant G6PD gene was isolated from the above selected strains by the following method.

The pCRBOSzwfM was introduced into the No. 58 strain by electroporation [*FEMS Microbiology Letters*, 65, 299 (1989)], and transformants were obtained by culturing the strain at 30° C. for 2 hours on KM163 agar medium [a medium containing 10 g of glucose, 10 g of Peptone (manufactured by Kyokuto Pharmaceutical), 5 g of Ehrlich meat extract (manufactured by Kyokuto Pharmaceutical), 2 g of urea, 2.5 g of sodium chloride and 18 g of Bacto-agar (manufactured by Difco) in 1 liter of water and adjusted to pH 7.23] containing 50 μg/ml kanamycin. A strain Tf1 as one of the transformants was selected, and the strain was cultured in KM163 medium containing 20 μg/ml kanamycin and subjected to electroporation to introduce pCGll (Japanese Patent Publication No. 91827/1994). After the introduction operation, the strain was cultured on KM163 agar medium containing 50 μg/ml kanamycin and 200 μg/ml spectinomycin at 30° C. for 2 days to obtain transformants. Chromosome of a strain from the transformants was examined by Southern blot hybridization according to the method of Ikeda et al. [*Microbiology*, 144, 1863 (1998)]. As a result, it was confirmed that the pCRBOSzwfM was integrated into the chromosome by a Campbell-type homologous recombination. Since the wild-type and mutant G6PD genes are closely located on the chromosome in those strains, second homologous recombination is apt to occur between them.

The transformant (single recombinant) was spread on a Suc medium [a medium containing 100 g of sucrose, 7 g of meat extract, 10 g of peptone, 3 g of sodium chloride, 5 g of Yeast extract (manufactured by Difco) and 18 g of Bacto-agar (manufactured by Difco) in 1 liter of water and adjusted to pH 7.2] and cultured at 30° C. for 1 day, and the surviving colonies were selected. A strain having the SacB gene cannot grow on this medium because it converts sucrose into a suicide substrate. On the other hand, a strain in which the SacB gene is deleted by the second homologous recombination between the wild-type and mutant G6PD genes can grow on this medium because the suicide substrate is not formed. During the homologous recombination, either the wild-type or mutant G6PD gene is deleted together with SacB. In this case, gene substitution into the mutant G6PD gene occurs in a strain in which the wild-type G6PD gene is deleted together with SacB.

A chromosomal DNA of the secondary recombinant obtained above was prepared by the method of Saito et al. [*Biochimica et Biophysica Acta*, 72, 619 (1963)], and PCR was carried out by using Pfu turbo DNA polymerase (manufactured by Stratagene) and the buffer attached thereto, wherein DNA fragments having the nucleotide sequences represented by SEQ ID NOs:3 and 4 were used as primers. Typing of the G6PD gene of the double recombinant in terms of wild-type or mutant was done by determining the nucleotide sequences of these PCR products in the usual way. As the results, it was confirmed that strains having only the wild-type G6PD gene (No. 58W strain as an example) and strains having only the mutant G6PD gene (No. 58M strain as an example) were obtained.

(4) L-Lysine Production Test

Lysine productivity of the thus obtained G6PD gene-substituted strains (No. 58W and No. 58M) and the No. 58 strain as the parent strain was evaluated by culturing them using a 5 liter-jar fermentor.

Each strain was inoculated into 100 ml of a first seed medium [a medium prepared by dissolving 50 g of glucose, 10 g of Yeast extract (manufactured by Nihon Pharmaceutical), 10 g of Peptone (manufactured by Kyokuto Pharmaceutical Industry), 5 g of corn steep liquor, 2.5 g of sodium chloride, 3 g of urea and 50 μg of biotin in 1 liter of water, adjusting the solution to pH 7.2, and further adding 10 g of calcium carbonate), and cultured at 30° C. for 24 hours in a 1 liter capacity Erlenmeyer flask with baffles. Next, 40 ml of the first seed broth was inoculated into 2,000 ml of a second seed medium (a medium prepared by dissolving 50 g of glucose, 10 g of corn steep liquor, 0.5 g of magnesium sulfate heptahydrate, 5 mg of nicotinic acid, 1 mg of thiamin hydrochloride, 100 μg of biotin, 10 mg of calcium pantothenate, 2 g of potassium dihydrogenphosphate, 3 g of urea, 10 mg of ferrous sulfate heptahydrate, 1 mg of zinc sulfate heptahydrate, 8 g of ammonium sulfate, 20 g of peptone and 2 g of sodium bicarbonate in 1 liter of water), and cultured at 30° C. for 12 hours in a 5 liter-jar fermentor. Next, 230 ml of the second seed broth was inoculated into 1,675 ml of a main culture medium [a medium prepared by dissolving 93 g of blackstrap molasses (sugar equivalent amount), 0.5 g of potassium dihydrogenphosphate, 10 mg of ferrous sulfate heptahydrate, 100 μg of thiamin hydrochloride, 2 g of soy peptone, 0.5 g of magnesium sulfate heptahydrate, 5 mg of nicotinic acid and 15 g of ammonium sulfate in 1 liter of water, and adjusted the pH to 7.4], and cultured at 35° C. for 42 hours in a 5 liter-jar fermentor.

The amount of L-lysine accumulated in the main culture was quantified by high performance liquid chromatography (HPLC).

Table 1 shows results of the measurement of the amount of L-lysine produced by the No. 5.8 strain, No. 58W strain and No. 58M strain. The results show that the L-lysine productivity is improved by the novel mutant C6PD.

TABLE 1

| Strain  | L-Lysine productivity (g/l) |
|---------|-----------------------------|
| No. 58  | 49.7                        |
| No. 58W | 53.5                        |
| No. 58M | 63.3                        |

INDUSTRIAL APPLICABILITY

According to the present invention, a modified G6PD and a DNA encoding the G6PD are obtained, and the productivity of L-amino acid by a microorganism can be improved by using the modified G6PD.

Free Text of Sequence Listing:

SEQ ID NO:3: Description of artificial sequence—Synthetic DNA

SEQ ID NO:4: Description of artificial sequence—Synthetic DNA

SEQ ID NO:5: Description of artificial sequence—Synthetic DNA

SEQ ID NO:6: Description of artificial sequence—Synthetic DNA

SEQ ID NO:7: Description of artificial sequence—Synthetic DNA

SEQ ID NO:8: Description of artificial sequence—Synthetic DNA

SEQ ID NO:9: Description of artificial sequence—Synthetic DNA

SEQ ID NO:10: Description of artificial sequence—Synthetic DNA

The invention claimed is:

1. An isolated or purified DNA which encodes a polypeptide selected from the group consisting of (a) to (d):
   (a) a polypeptide which consists of SEQ ID NO:2,
   (b) a polypeptide which consists of a variant of SEQ ID NO:2, wherein only Ala at position 213 in SEQ ID NO:2 is replaced with another amino acid, and a variant of SEQ ID NO:2, wherein glucose-6-phosphate dehydrogenase activity,
   (c) a polypeptide which consists of SEQ ID NO:12, and
   (d) a polypeptide which consists of a variant of SEQ ID NO:12, wherein up to ten amino acids other than the amino acid residue at position 213 in SEQ ID NO:12 are deleted, substituted or added, and a variant of SEQ ID NO:12, has glucose-6-phosphate dehydrogenase activity.

2. An isolated or purified DNA which consists of the nucleotide sequence SEQ ID NO:1.

3. An isolated or purified DNA which consists of a variant of SEQ ID NO:1, wherein only positions 637 to 639 in the nucleotide sequence of SEQ ID NO:1 is replaced with a codon encoding an amino acid other than Ala and wherein said variant encodes a polypeptide with glucose-6-phosphate dehydrogenase activity.

4. An isolated or purified DNA which consists of the nucleotide sequence SEQ ID NO:11.

5. An isolated or purified DNA which hybridizes with a DNA comprising the nucleotide sequence of SEQ ID NO:1 at 65° C. in the presence of 0.7 to 1.0 mol/l of sodium chloride using a filter on which colony- or plaque-derived DNA is immobilized, followed by washing at 65° C. with 0.1 to 2×SSC solution, and encodes a polypeptide having glucose-6-phosphate dehydrogenase activity,
   wherein a nucleotide sequence corresponding to the nucleotide sequence of positions 637 to 639 encoding in the nucleotide sequence SEQ ID NO:1 is replaced with a codon encoding an amino acid other than Ala and an amino acid sequence of the polypeptide encoded by the hybridizable DNA has homology of 95% or more compared with the amino acid sequence of SEQ ID NO:12.

6. An isolated or purified DNA which hybridizes with a DNA comprising the nucleotide sequence of SEQ ID NO:1 at 65° C. in the presence of 0.7 to 1.0 mol/l of sodium chloride using a filter on which colony- or plaque-derived DNA is immobilized, followed by washing at 65° C. with 0.1 to 2×SSC solution, and encodes a polypeptide having glucose-6-phosphate dehydrogenase activity,
wherein a nucleotide sequence corresponding to the nucleotide of position 637 in the nucleotide sequence SEQ ID NO:1 is replaced with adenine and an amino acid sequence of the polypeptide encoded by the hybridizable DNA has homology of 95% or more compared with the amino acid sequence of SEQ ID NO:12.

7. A recombinant DNA which is obtained by inserting the DNA according to any one of claims 1 to 6 into a vector.

8. The recombinant DNA according to claim 7, wherein the recombinant DNA is replicates in a microorganism belonging to the genus *Escherichia* or the genus *Corynebacterium*.

9. A plasmid pCRBzwfM found in *Escherichia coli* TOP10 (FERM BP-7135).

10. A transformant which is obtained by introducing the recombinant DNA according to claim 8 into a host cell.

11. The transformant according to claim 10, wherein the host cell is a microorganism which produces L-amino acids.

12. The transformant according to claim 11, wherein the host cell belongs to the genus *Escherichia* or the genus *Corynebacterium*.

13. A transformant belonging to the genus *Escherichia* or the genus *Corynebacterium*, which comprises a genome into which the DNA according to any one of claims 3 to 6 is integrated.

14. The transformant according to claim 13, wherein the host cell is *Corynebacterium glutamicum*.

15. A process for producing a polypeptide, which comprises culturing the transformant according to claim 11 in a medium to form and accumulate in culture a polypeptide selected from the group consisting of (a) to (d):
(a) a polypeptide which consists of SEQ ID NO:2,
(b) a polypeptide which consists of a variant of SEQ ID NO:2, wherein only Ala at position 213 in SEQ ID NO:2 is replaced with another amino acid, and said variant of SEQ ID NO:2 has glucose-6-phosphate dehydrogenase activity,
(c) a polypeptide which consists of SEQ ID NO:12, and
(d) a polypeptide which consists of a variant of SEQ ID NO:12, wherein up to ten amino acids other than the amino acid residue at position 213 in SEQ ID NO:12 are deleted, substituted or added, and said variant of SEQ ID NO:12 has glucose-6-phosphate dehydrogenase activity, and
recovering the polypeptide from the culture.

16. A process for producing L-lysine, L-threonine, L-isoleucine, L-tryptophan, L-phenylalanine, L-tyrosine, L-histidine or L-cysteine, which comprises culturing the transformant according to claim 11 in a medium to form and accumulate the L-amino acid which is biosynthesized using NADPH in the culture and said recombinant DNA or transformant and recovering the L-amino acid from the culture.

17. The process for producing L-amino acid according to claim 16, wherein the L-amino acid is L-lysine.

* * * * *

UNITED STATES PATENT AND TRADEMARK OFFICE
CERTIFICATE OF CORRECTION

PATENT NO.        : 7,078,204 B2
APPLICATION NO.   : 10/312007
DATED             : July 18, 2006
INVENTOR(S)       : Haruhiko Yokoi et al.

It is certified that error appears in the above-identified patent and that said Letters Patent is hereby corrected as shown below:

COLUMN 1:

Line 48, "[EC-1.1.1.41]" should read --[EC 1.1.1.41]--.

COLUMN 2:

Line 24, "to(23)." should read --to (23).--.

COLUMN 3:

Line 50, "amino-acid" should read --amino acid--.

COLUMN 6:

Line 29, "chiais" should read --chia is--;
    Line 31, "manhein)," should read --manheim),--;
    Line 41, "(FERM-BP-5408]," should read --(FERM BP-5408)]--; and
    Line 42, "chia coli IGH2" should read --chia coli IGHA2--.

COLUMN 7:

Line 40, "corynebacterium" should be deleted; and
    Line 41, "glutamicum ATCC 13869" should be deleted.

COLUMN 8:

Line 58, "dipotassium:" should read --dipotassium--.

COLUMN 9:

Line 27, "altrasonicator" should read --ultrasonicator--.

COLUMN 10:

Line 20, "coil." should read --coli--;
    Line 44, "gene" should read --genes--; and
    Line 61, "attached-buffer." should read --attached buffer.--.

UNITED STATES PATENT AND TRADEMARK OFFICE
CERTIFICATE OF CORRECTION

| | |
|---|---|
| PATENT NO. | : 7,078,204 B2 |
| APPLICATION NO. | : 10/312007 |
| DATED | : July 18, 2006 |
| INVENTOR(S) | : Haruhiko Yokoi et al. |

It is certified that error appears in the above-identified patent and that said Letters Patent is hereby corrected as shown below:

COLUMN 11:

Line 63, "Deposatory" should read --Depository--; and "Advanced" should read --Advanced Industrial--.

COLUMN 14:

Line 49, "(Oric)" should read --(OriC)--.

COLUMN 15:

Line 15, "Oric" should read --OriC--; and
      Line 47, "pH 7.23]" should read --pH 7.2]--.

COLUMN 16:

Line 39, "carbonate)," should read --carbonate],--;
      Line 49, "I liter" should read --1 liter--;
      Line 65, "No. 5.8 strain," should read --No. 58 strain,--; and
      Line 67, "C6PD." should read --G6PD.--.

COLUMN 31:

Line 55, "a" should read --said--;
      Line 56, "SEQ ID NO:2, wherein" should read --SEQ ID NO:2 has--;
      Line 62, "a" should read --said--; and
      Line 63, "ID NO:12," should read --ID NO:12--.

COLUMN 32:

Line 65, "encoding" should be deleted.

COLUMN 33:

Line 22, "is" should be deleted; and
      Line 36, "claim 3" should read --claim 1--.

UNITED STATES PATENT AND TRADEMARK OFFICE
CERTIFICATE OF CORRECTION

PATENT NO. : 7,078,204 B2
APPLICATION NO. : 10/312007
DATED : July 18, 2006
INVENTOR(S) : Haruhiko Yokoi et al.

It is certified that error appears in the above-identified patent and that said Letters Patent is hereby corrected as shown below:

SHEET 2:

Figure 2, "DLETION" should read --DELETION--.

Signed and Sealed this

Sixteenth Day of January, 2007

JON W. DUDAS
*Director of the United States Patent and Trademark Office*